(12) United States Patent
DiPoto et al.

(10) Patent No.: US 7,766,930 B2
(45) Date of Patent: *Aug. 3, 2010

(54) CANNULA FOR RECEIVING SURGICAL INSTRUMENTS

(75) Inventors: Gene P. DiPoto, Upton, MA (US); Alan E. Shluzas, West Roxbury, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1893 days.

This patent is subject to a terminal disclaimer.

(21) Appl. No.: 10/686,063

(22) Filed: Oct. 15, 2003

(65) Prior Publication Data

US 2004/0097907 A1 May 20, 2004

Related U.S. Application Data

(60) Division of application No. 10/361,887, filed on Feb. 10, 2003, now Pat. No. 7,144,393, which is a continuation-in-part of application No. 09/855,358, filed on May 15, 2001, now Pat. No. 6,524,320.

(51) Int. Cl.
*A61B 17/00* (2006.01)
*A61B 29/00* (2006.01)
(52) U.S. Cl. ..................... 606/191; 606/108
(58) Field of Classification Search .............. 606/108, 606/61, 71, 191, 198
See application file for complete search history.

(56) References Cited

U.S. PATENT DOCUMENTS

| 151,228 A | 5/1874 | Knaffl |
| 530,728 A | 12/1894 | Sherbrook |

(Continued)

FOREIGN PATENT DOCUMENTS

DE 202 16 712 U 1 3/2003

(Continued)

OTHER PUBLICATIONS

Atlantis Surgical, Jakoscope® Minimally Invasive Direct Access Surgical Technology, leaflet 1998.

(Continued)

*Primary Examiner*—Vy Q Bui
(74) *Attorney, Agent, or Firm*—Crompton, Seager & Tufte, LLC.

(57) ABSTRACT

A cannula (10) for receiving surgical instruments for performing a surgical procedure on a body includes a tubular structure (12) defining a passage (16) through which the surgical instruments are inserted into the body. The tubular structure (12) includes an expandable portion (40) for enabling an increase in the cross-sectional area of the passage (16). The expandable portion (40) of the tubular structure (12) has a slot (100) and a guide member (114) disposed in the slot. The guide member (114) is movable from a first end (102) of the slot (100) toward a second end (104) of the slot to enable the cross-sectional area of the passage (16) to increase. The expandable portion (40) has a stop (106) between the first and second ends (102 and 104) of the slot (100) engageable with the guide member (114) to retain the guide member in a position relative to the slot and resist movement of the guide member from the position relative to the slot.

29 Claims, 7 Drawing Sheets

U.S. PATENT DOCUMENTS

| | | | |
|---|---|---|---|
| 1,170,324 A | 2/1916 | Pomerene |
| 2,083,573 A | 6/1937 | Morgan |
| 2,313,164 A | 3/1943 | Nelson |
| 2,594,086 A | 4/1952 | Smith |
| 2,623,517 A | 12/1952 | Barlow et al. |
| 3,044,461 A | 7/1962 | Murdock |
| 3,070,088 A | 12/1962 | Brahos |
| 3,503,398 A | 3/1970 | Fogarty et al. |
| 3,509,873 A | 5/1970 | Karlin et al. |
| 3,749,088 A | 7/1973 | Kohlmann |
| 3,789,852 A | 2/1974 | Kim et al. |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,155,355 A | 5/1979 | Yamamoto |
| 4,254,763 A | 3/1981 | McCready et al. |
| 4,421,107 A | 12/1983 | Estes et al. |
| 4,449,532 A | 5/1984 | Storz |
| 4,451,256 A | 5/1984 | Weikl et al. |
| 4,545,374 A | 10/1985 | Jacobson |
| 4,573,448 A | 3/1986 | Kambin |
| 4,601,713 A | 7/1986 | Fuqua |
| 4,716,901 A | 1/1988 | Jackson et al. |
| 4,863,133 A | 9/1989 | Bonnell |
| 4,899,729 A | 2/1990 | Gill et al. |
| 4,921,478 A | 5/1990 | Solano et al. |
| 4,984,564 A | 1/1991 | Yuen |
| 5,139,511 A | 8/1992 | Gill et al. |
| 5,163,949 A | 11/1992 | Bonutti |
| 5,183,464 A | 2/1993 | Dubrul et al. |
| 5,190,561 A | 3/1993 | Graber |
| 5,196,023 A | 3/1993 | Martin |
| 5,197,971 A | 3/1993 | Bonutti |
| 5,231,974 A | 8/1993 | Giglio et al. |
| 5,295,994 A | 3/1994 | Bonutti |
| 5,312,417 A | 5/1994 | Wilk |
| 5,313,962 A | 5/1994 | Obenchain |
| 5,318,588 A | 6/1994 | Horzewski et al. |
| 5,345,927 A | 9/1994 | Bonutti |
| 5,354,302 A | 10/1994 | Ko |
| 5,370,647 A | 12/1994 | Graber et al. |
| 5,370,659 A | 12/1994 | Sakashita |
| 5,395,317 A | 3/1995 | Kambin |
| 5,400,774 A | 3/1995 | Villalta et al. |
| 5,417,203 A | 5/1995 | Tovey et al. |
| 5,439,464 A | 8/1995 | Shapiro |
| 5,443,479 A | 8/1995 | Bressi, Jr. |
| 5,454,365 A | 10/1995 | Bonutti |
| 5,490,819 A | 2/1996 | Nicholas et al. |
| 5,503,617 A | 4/1996 | Jako |
| 5,505,690 A | 4/1996 | Patton et al. |
| 5,529,571 A | 6/1996 | Daniel |
| 5,573,517 A | 11/1996 | Bonutti et al. |
| 5,601,590 A | 2/1997 | Bonutti et al. |
| 5,601,690 A | 2/1997 | Gauld et al. |
| 5,667,481 A | 9/1997 | Villalta et al. |
| 5,667,520 A | 9/1997 | Bonutti |
| 5,681,265 A | 10/1997 | Maeda et al. |
| 5,688,223 A | 11/1997 | Rosendahl |
| 5,690,606 A | 11/1997 | Slotman |
| 5,707,359 A | 1/1998 | Bufalini |
| 5,728,046 A | 3/1998 | Mayer et al. |
| 5,762,629 A | 6/1998 | Kambin |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,813,978 A | 9/1998 | Jako |
| 5,827,319 A | 10/1998 | Carlson et al. |
| 5,851,214 A | 12/1998 | Larsen et al. |
| 5,865,802 A | 2/1999 | Yoon et al. |
| 5,868,668 A | 2/1999 | Weiss |
| 5,902,231 A | 5/1999 | Foley et al. |
| 5,944,658 A | 8/1999 | Koros et al. |
| 5,954,635 A | 9/1999 | Foley et al. |
| 5,961,499 A | 10/1999 | Bonutti et al. |
| 5,976,146 A | 11/1999 | Ogawa et al. |
| 5,976,161 A | 11/1999 | Kirsch et al. |
| 5,997,508 A | 12/1999 | Lunn et al. |
| 6,024,697 A | 2/2000 | Pisarik |
| 6,083,154 A | 7/2000 | Liu et al. |
| 6,096,046 A | 8/2000 | Weiss |
| 6,120,437 A | 9/2000 | Yoon et al. |
| 6,126,671 A | 10/2000 | Richards et al. |
| 6,139,493 A | 10/2000 | Koros et al. |
| 6,152,871 A | 11/2000 | Foley et al. |
| 6,162,236 A | 12/2000 | Osada |
| 6,171,299 B1 | 1/2001 | Bonutti |
| 6,175,758 B1 | 1/2001 | Kambin |
| 6,187,000 B1 | 2/2001 | Davison et al. |
| 6,206,826 B1 | 3/2001 | Mathews et al. |
| 6,224,545 B1 | 5/2001 | Cocchia et al. |
| 6,312,443 B1 | 11/2001 | Stone |
| 6,338,730 B1 | 1/2002 | Bonutti et al. |
| 6,354,995 B1 | 3/2002 | Hoftman et al. |
| 6,358,266 B1 | 3/2002 | Bonutti |
| 6,361,488 B1 | 3/2002 | Davison et al. |
| 6,371,968 B1 * | 4/2002 | Kogasaka et al. ........... 606/190 |
| 6,383,195 B1 | 5/2002 | Richard |
| 6,464,634 B1 | 10/2002 | Fraser |
| 6,494,893 B2 | 12/2002 | Dubrul et al. |
| 6,524,320 B2 | 2/2003 | DiPoto |
| 6,530,880 B2 | 3/2003 | Pagliuca |
| 6,530,926 B1 | 3/2003 | Davison |
| 6,575,899 B1 * | 6/2003 | Foley et al. ................. 600/114 |
| 6,616,605 B2 | 9/2003 | Wright et al. |
| 6,648,888 B1 | 11/2003 | Shluzas |
| 6,652,553 B2 | 11/2003 | Davison et al. |
| 6,712,795 B1 | 3/2004 | Cohen |
| 6,800,084 B2 | 10/2004 | Davison et al. |
| 6,821,243 B2 | 11/2004 | Pagliuca et al. |
| 6,837,889 B2 | 1/2005 | Shluzas |
| 7,001,397 B2 | 2/2006 | Davison et al. |
| 7,004,947 B2 | 2/2006 | Shluzas et al. |
| 7,056,321 B2 | 6/2006 | Pagliuca et al. |
| 7,066,937 B2 | 6/2006 | Shluzas |
| 7,144,393 B2 | 12/2006 | DiPoto et al. |
| 7,223,278 B2 | 5/2007 | Davison et al. |
| 2001/0049498 A1 | 12/2001 | Davison et al. |
| 2002/0002360 A1 | 1/2002 | Orth et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. ............. 600/102 |
| 2003/0073998 A1 | 4/2003 | Pagliuca et al. ............... 606/61 |
| 2003/0097045 A1 | 5/2003 | Kashyap |
| 2003/0153911 A1 | 8/2003 | Shluzas ....................... 606/61 |
| 2003/0153927 A1 | 8/2003 | DiPoto et al. ............... 606/108 |
| 2003/0167058 A1 | 9/2003 | Shluzas ....................... 606/61 |
| 2003/0191371 A1 | 10/2003 | Smith et al. |
| 2003/0195551 A1 | 10/2003 | Davison et al. |
| 2003/0236529 A1 | 12/2003 | Shluzas et al. ............... 606/105 |
| 2004/0002629 A1 | 1/2004 | Branch et al. |
| 2004/0093001 A1 | 5/2004 | Hamada |
| 2004/0176665 A1 | 9/2004 | Branch et al. |
| 2005/0137461 A1 | 6/2005 | Marchek et al. |
| 2005/0149106 A1 | 7/2005 | DiPoto et al. |
| 2005/0159650 A1 | 7/2005 | Raymond et al. |
| 2005/0159651 A1 | 7/2005 | Raymond et al. |
| 2007/0142857 A1 | 6/2007 | DiPoto et al. |

FOREIGN PATENT DOCUMENTS

| | | |
|---|---|---|
| EP | 0807415 A2 | 11/1997 |

| | | |
|---|---|---|
| WO | WO 95/22285 | 8/1995 |
| WO | WO 01/54560 A2 | 2/2001 |

OTHER PUBLICATIONS

Caspar, Wolfhard, M.D. et al., The Caspar Microsurgical Discectomy and Comparison with a Conventional Standard Lumbar Disc Procedure, Neurosurgery, vol. 28, Nov. 1, 1991.
Bookwalter Retractor Kit II, by Codman, Johnson & Johnson, 1997.
Balfour Retractors and Blades Catalog, 1997.
Jako, G.J. et al., Development of minimally invasive direct access surgical technology, The British Journal of Surgery, vol. 85, Supplement 2, Jul. 1998, pp. 208-210—Eurosurgery 98, Budapest, Hungary, Jun. 17-20, 1998, Blackwell Science.
Manual entitled MED™—MicroEndoscopic Discrectomy System by Sofamor Danek USA, dated 1996 (11. 1-33).
Ditsworth, David A., M.D., *Surg Neurol*, 49; 588-598, 1998 "Endoscopic Transforaminal Lumbar Discectomy and Reconfiguration: A Postero-lateral Approach into the Spinal Canal".
Endius Marketing Bulletin, 2002, Atavi Atraumatic Spine Fusion System "How do I decompress using Atavi System?".
Endius Marketing Bulletin, 2002, Atavi Atraumatic Spine Fusion System "Minimally Invasive Update on Danek".
Foley, Kevin T., M.D., Gupta, Sanjay K., M.D., Justis, Jeff R., B.S., Sherman, Michael C., M.S., *Neurosurg Focus*, 10: 1-8, 2001 "Percutaneous pedicle screw fixation of the lumbar spine".
Guiot, Bernard H., M.D., Khoo, Larry T., M.D., Fessler, Richard G., M.D., Ph.D., *Spine*, 27, 4: 432-438, 2002 "A Minimally Invasive Technique for Decompression of the Lumbar Spine".
Kambin, Parviz, Publisher Unknown , Chapter 77, 1055-1066, Date Unknown "Arthroscopic Lumbar Interbody Fusion".
Kambin, Parviz, The Adult Spine: Principles and Practice, $2^{nd}$ edition; Lippincott-Raven, 2037-2046, 1997 "Arthroscopic Lumbar Intervertebral Fusion".
Kambin, Parviz, The Mount Sinai Journal of Medicine, 58, 2: 159-164, 1991 "Arthroscopic Microdiskectomy".
Kambin, Parviz, Operativ Arthrosc py, Second Edition, 89:1215-1225, 1996 "Arthroscopic Techniques for Spinal Surgery".
Kambin, Parviz, *Neurosurgery Clinics of North America*, 7(1): 65-76, 1996 "Diagnostic and Therapeutic Spinal Arthroscopy".
Kambin, Parviz, Publisher Unknown, Chapter 9:117-121, Date Unknown "Posterolateral Percutaneous Lumbar Interbody Fusion".
Kambin, Parviz, *Advances in Operative Orthopaedics*, 3:147-171, 1995 "The Role of Minimally Invasive Surgery in Spinal Disorders".
Medtronic Sofamor Danek, *METRx MicroEndoscopic Discectomy*, 1999 "An Evolution in Minimally Invasive Spine Surgery".
Medtronic Sofamor Danek, *METRx MicroDiscectomy System*, 2000 "The Next Step in Minimally Invasive Discectomy Utilizing the Operating Microscope".
Medtronic Sofmor Danek, *METRx Microdiscectomy Surgical Technique*, 2001 as described by: Donald L. Hilton, Jr., M.D., F.A.C.S. and Sylvain Palmer, M.D., F.A.C.S.
Medtronic Sofamor Danek, *Orthopedics Today*, 1-20, 2002 "Minimal Access Spinal Technologies".
Stauber, Martin H., M.D., Bassett, George S., M.D., *SPINE*, 19, 1: 57-61, 1994 "Pedicle Screw Placement With Intraosseous Endoscopy".
Howard, "Minimal and Direct Access to the Anterior Lumbar Spine," Spinal Surgery; Anterior Lumbar Interbody Fusion: (ALIF) with the Howard/Jako-MIDAST Concept and Method, 20 pgs., 1996-1997.
Jako et al., "Minimally Invasive Direct Access Surgical Technology—MIDAST," General Surgery, Surgical Technology VIII, 111-119, on or before Feb. 10, 2003.
Warnock, "Jakoscope Allows Better View, Smaller Incisions for ALIF," Orthopedics Today, 3 pgs., on or before Feb. 10, 2003.
Co-pending U.S. Appl. No. 10/440,231, filed May 16, 2003, titled Cannula for receiving surgical instruments, and assigned to the assignee of this application.
Co-pending U.S. Appl. No. 10/441,319, filed May 16, 2003, titled Cannula for receiving surgical instruments, and assigned to the assignee of this application.
Co-pending U.S. Appl. No. 10/440,002, filed May 16, 2003, titled Cannula for receiving surgical instruments, and assigned to the assignee of this application.
Co-pending U.S. Appl. No. 10/440,278, filed May 16, 2003, titled Cannula for receiving surgical instruments, and assigned to the assignee of this application.
Co-pending U.S. Appl. No. 10/439,979, filed May 16, 2003, titled Cannula for receiving surgical instruments, and assigned to the assignee of this application.
Co-pending U.S. Appl. No. 10/439,385, filed May 16, 2003, titled Cannula for receiving surgical instruments, and assigned to the assignee of this application.
Co-pending U.S. Appl. No. 10/435,730, filed May 9, 2003, titled Method for performing a surgical procedure and a cannula for use in performing the surgical procedure, and assigned to the assignee of this application.
Co-pending U.S. Appl. No. 10/713,820, filed Nov. 14, 2003, titled Cannula for receiving surgical instruments, and assigned to the assignee of this application.
Co-pending U.S. Appl. No. 10/686,154, filed Oct. 15, 2003, titled Method of securing vertebrae, and assigned to the assignee of this application.
Co-pending U.S. Appl. No. 10/678,744, filed Oct. 2, 2003, titled Minimally invasive access device and method, and assigned to the assignee of this application.
Co-pending U.S. Appl. No. 10/658,736, filed Sep. 9, 2003, titled Methods and apparatuses for treating the spine through an access device, and assigned to the assignee of this application.
Co-pending U.S. Appl. No. 09/772,605, filed Jan. 30, 2001, titled Method for performing a surgical procedure and a cannula for use in performing the surgical procedure, and assigned to the assignee of this application.
Amendment to U.S. Appl. No. 09/772,605, filed Jan. 30, 2001, Office Action dated Oct. 31, 2003, Response to Office Action filed Feb. 2, 2004.

* cited by examiner

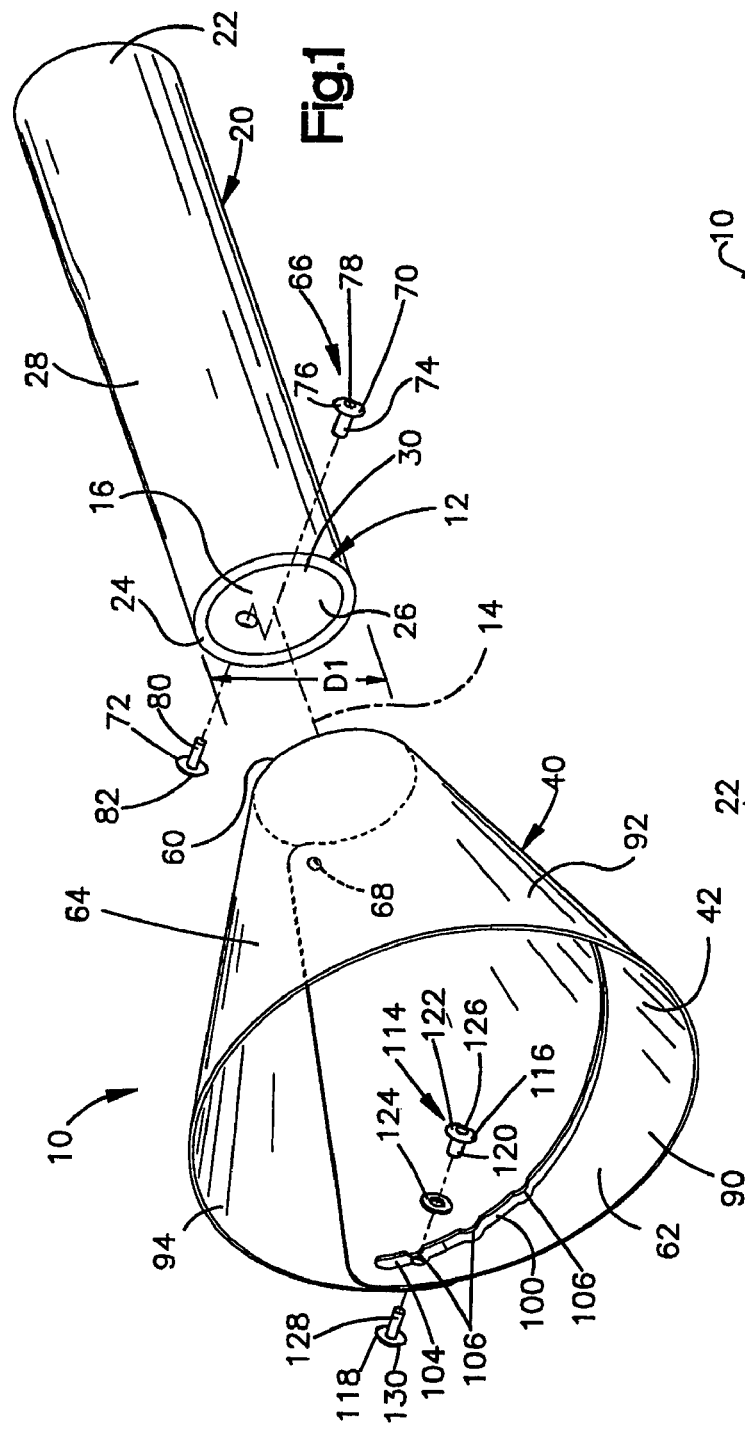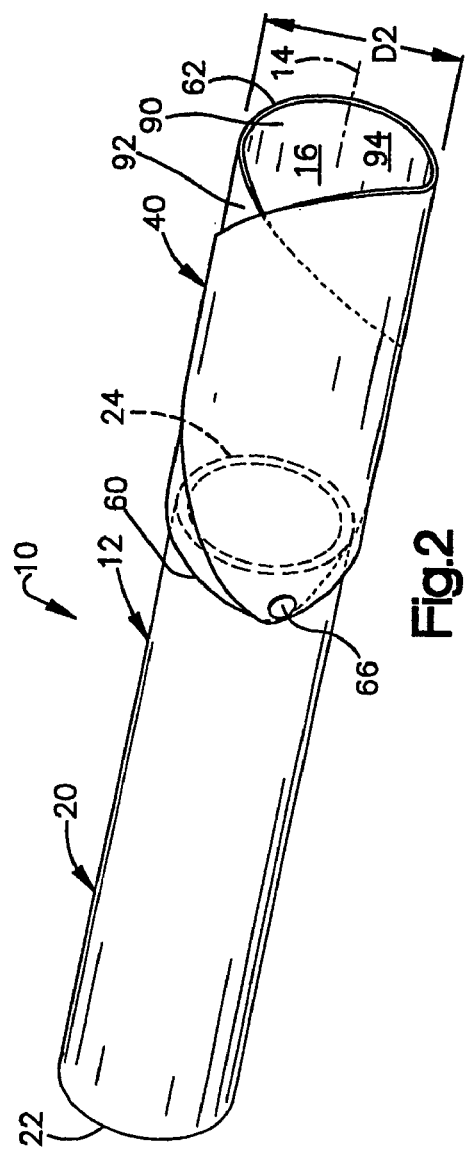

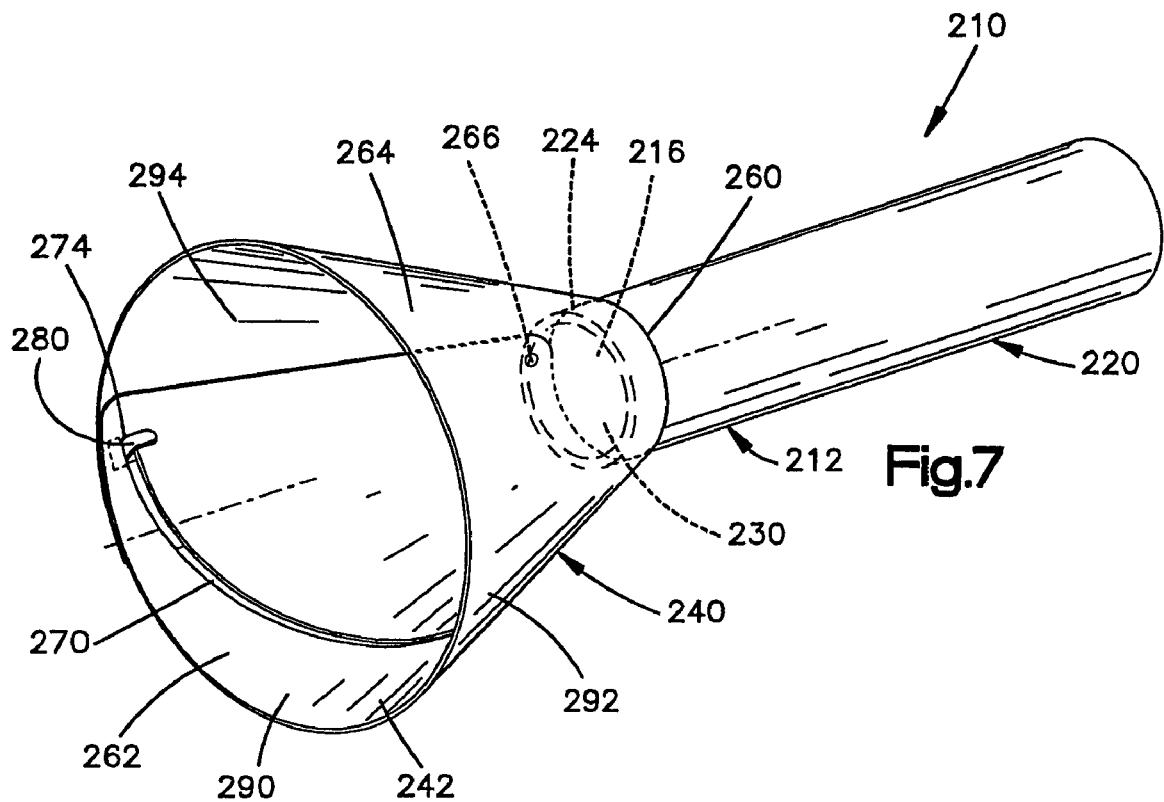
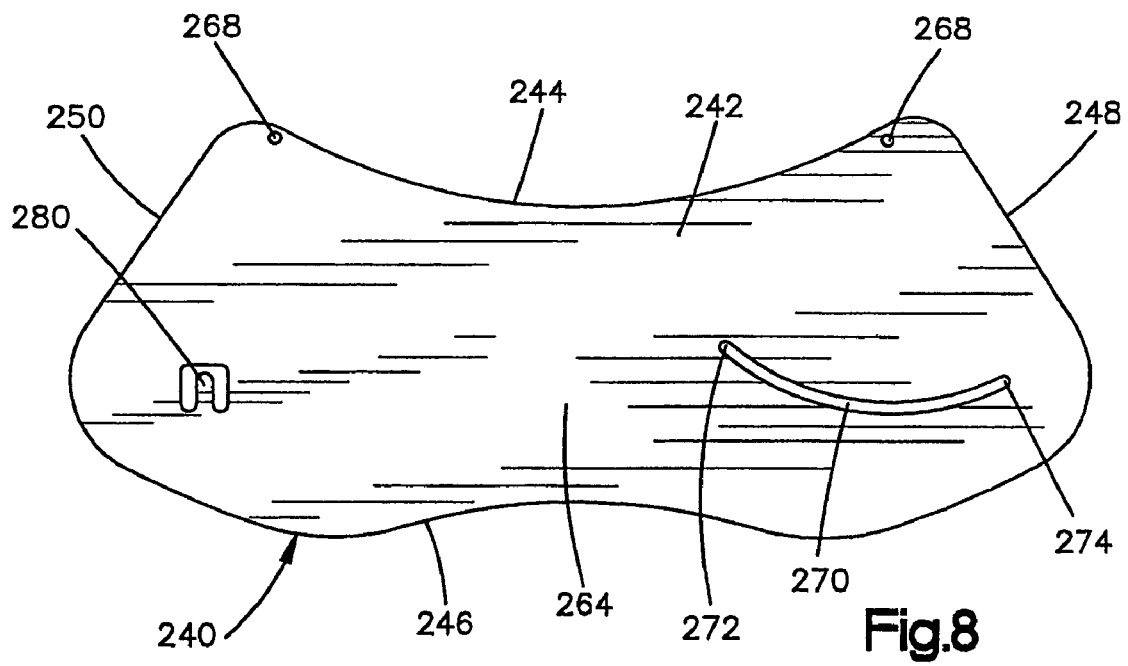

CANNULA FOR RECEIVING SURGICAL INSTRUMENTS

RELATED APPLICATIONS

This application is a divisional of U.S. application Ser. No. 10/361,887, filed Feb. 10, 2003, now U.S. Pat. No. 7,144,393 which is a continuation-in-part of U.S. application Ser. No. 09/855,358, filed May 15, 2001, now U.S. Pat. No. 6,524,320.

FIELD OF THE INVENTION

The present invention relates to a cannula for receiving surgical instruments for performing a surgical procedure on a body.

BACKGROUND OF THE INVENTION

A known cannula for receiving surgical instruments is disclosed in U.S. Pat. No. 6,187,000. U.S. Pat. No. 6,187,000 discloses a cannula having an expandable portion. The expandable portion has a slot and a guide member disposed in the slot. The guide member is movable from a first terminal end of the slot to a second terminal end of the slot to enable the cross-sectional area of a passage in the cannula to increase.

SUMMARY OF THE INVENTION

The present invention is a cannula for receiving surgical instruments for performing a surgical procedure on a body. The cannula includes a tube structure defining a passage through which the surgical instruments are inserted into the body. The tube structure includes an expandable portion for enabling an increase in the cross-sectional area of the passage.

The expandable portion of the tube structure has a slot and a guide member disposed in the slot. The guide member is movable from a first end of the slot toward a second end of the slot to enable the cross-sectional area of the passage to increase. The expandable portion has a stop between the first and second ends of the slot engageable with the guide member. The stop retains the guide member in a position relative to the slot and resists movement of the guide member relative to the slot from the position.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is an exploded perspective view of a surgical cannula constructed in accordance with a first embodiment of the present invention, the cannula being shown in an expanded condition;

FIG. 2 is a perspective view of the cannula of FIG. 1, the cannula being shown in a contracted condition;

FIG. 7 is a schematic perspective view of a surgical cannula constructed in accordance with a second embodiment of the present invention, the cannula being shown in an expanded condition;

FIG. 8 is a rollout view of an arcuate segment of the cannula of FIG. 7;

DESCRIPTION OF THE INVENTION

Figure 3:
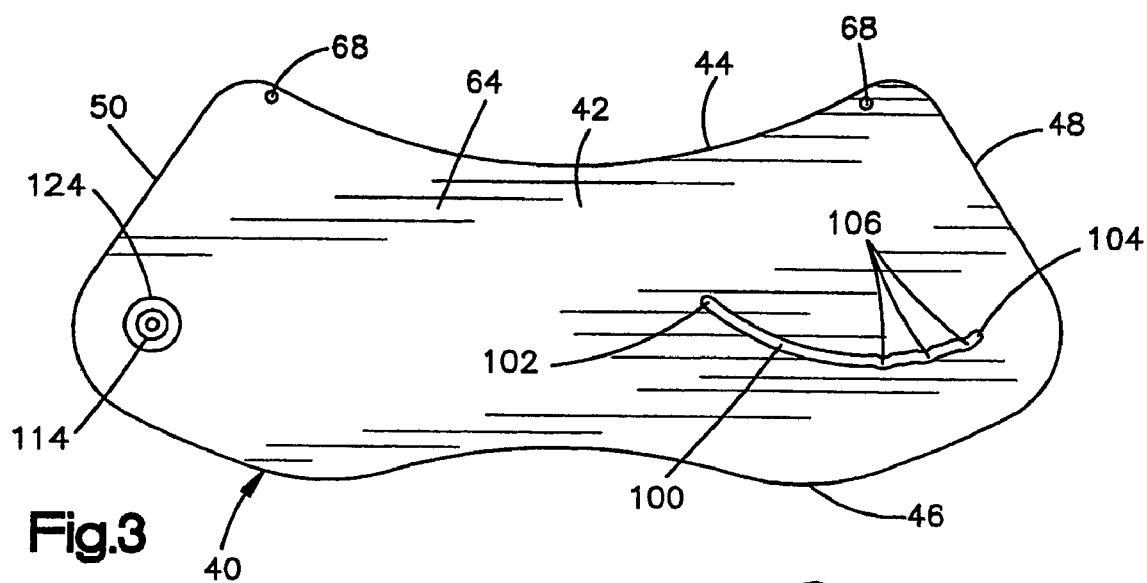
FIG. 3 is a rollout view of an arcuate segment of the cannula of FIG. 1.

The present invention is directed to a cannula for receiving surgical instruments during a surgical procedure. The present invention is applicable to a variety of surgical procedures in which endoscopic surgical techniques are used.

FIG. 1 illustrates a cannula 10 constructed according to a first embodiment of the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material, such as a radiolucent material. The first tubular portion 20 has a proximal end 22 and a distal end 24. Parallel cylindrical inner and outer surfaces 26 and 28 extend between the ends 22, 24 of the first tubular portion 20. The first tubular portion 20 has a thickness measured perpendicular to the surfaces 26 and 28 in the range of 0.02 inches to 0.04 inches or approximately 0.5 mm to approximately 1.0 mm.

The inner surface 26 (FIG. 1) defines a first passage portion 30 of the passage 16 through the cannula 10. The first passage portion 30 has a diameter D1 which is preferably in the range from 10 mm to 20 mm or approximately 0.4 inches to approximately 0.8 inches. The inner surface 26 may have a non-reflective coating to reduce glare on any video image produced by a video camera inserted through the passage 16.

The second tubular portion 40 of the tubular structure 12 is attached to the distal end 24 of the first tubular portion 20. The second tubular portion 40 is preferably made from stainless steel, but could alternatively be made from another suitable material, such as a radiolucent material.

As best seen in the rollout view of FIG. 3, the second tubular portion 40 includes an arcuate segment 42 of sheet stock. The arcuate segment 42 includes first and second edges 44 and 46. The arcuate segment 42 also includes first and second planar edges 48 and 50 extending between the edges 44 and 46. The first and second planar edges 48 and 50 are rolled in an overlapping manner to form the tubular configuration of the second tubular portion 40.

When the second tubular portion 40 (FIG. 1) has been rolled into its tubular configuration, the first and second edges 44 and 46 define oppositely disposed first and second ends 60 and 62 of the second tubular portion. The first and second ends 60 and 62 are connected by a central portion 64. The first end 60 of the second tubular portion 40 is attached to the distal end 24 of the first tubular portion 20 by a suitable fastener, such as a rivet 66. It is contemplated that a screw could be used instead of the rivet 66. The rivet 66 extends through two aligned apertures 68 at the first end 60 of the second tubular portion 40.

The rivet 66 has a first portion 70 and a second portion 72. The first portion 70 has a shaft 74 extending from a head 76. The shaft 74 extends through the apertures 68 in the tubular portion 40 and the head 76 engages the inner surface 26 of the first tubular portion 20. A cylindrical opening 78 extends through the shaft 74 and the head 76.

The second portion 72 of the rivet 66 has a shaft 80 extending from a head 82. The shaft 80 extends into the opening 78 in the first portion 68 of the rivet 66 and the head 82 engages the second tubular portion 40. The shaft 80 of the second portion 72 extends into the opening 78 in the first portion 70 to connect the first and second portions of the rivet 66 and pivotally connect the second tubular portion 40 to the first tubular portion 20.

The second tubular portion 40 (FIG. 1) includes parallel inner and outer surfaces 90 and 92 extending between the first and second ends 60 and 62. The inner surface 90 defines a second passage portion 94 of the passage 16 through the cannula 10 which extends as a continuation of the first passage portion 30 in the first tubular portion 20. The second tubular portion 40 has a thickness measured perpendicular to the surfaces 90 and 92 in the range of 0.003 inches to 0.005 inches or approximately 0.075 mm to approximately 0.125 mm. The inner surface may have a non-reflective coating that reduces glare on any video image produced by a camera inserted through the passage 16.

An arcuate slot 100 (FIGS. 1 and 3) is formed in the second tubular portion 40 and extends between the inner and outer surfaces 90 and 92 of the second tubular portion. The arcuate slot 100 extends in a direction along a curvilinear path in the central portion 64 of the second tubular portion 40 toward the end 62 of the second tubular portion. The arcuate slot 100 has a first end 102 located in the central portion 64 of the second tubular portion 40. A second end 104 of the arcuate slot 100 is located adjacent the intersection of the second edge 46 and the planar edge 48 of the arcuate segment 42.

Figure 4:
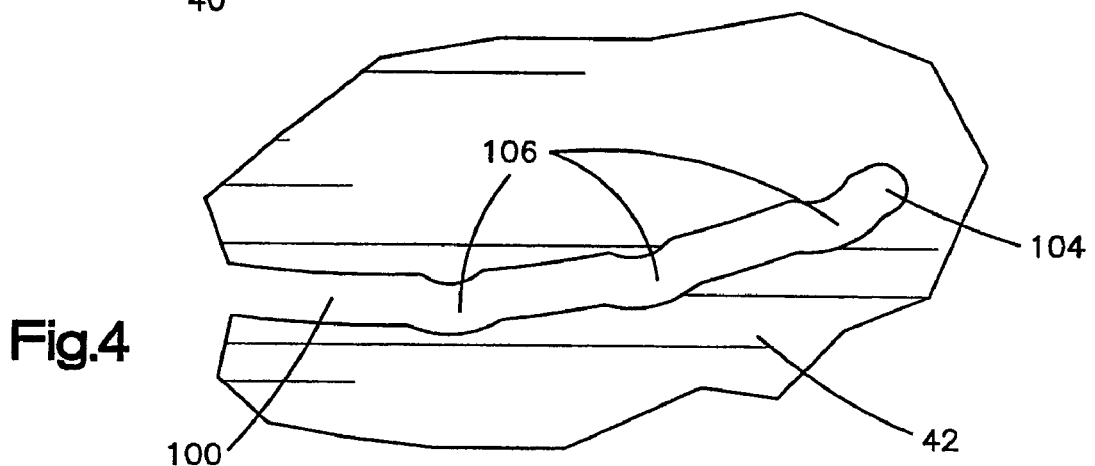
FIG. 4 is an enlarged view of a slot in the arcuate segment of FIG. 3.

The arcuate slot 100 (FIGS. 3 and 4) has three notches or stops 106 between the ends 102 and 104. The notches 106 define three expanded conditions of the second tubular portion 40. The notches 106 extend in directions transverse to the arcuate direction in which the slot 100 extends. Although the present invention shows three stops 106, it is contemplated that the slot could have any number of stops.

A guide member or rivet 114 (FIGS. 1 and 3) is attached to the inner surface 90 of the second tubular portion 40 adjacent the intersection of the second edge 46 and the planar edge 50. It is contemplated that a guide pin or screw could be used instead of the rivet 114. In the tubular configuration of the second tubular portion 40, the guide member 114 is located in the arcuate slot 100 and is movable along the curvilinear path of the arcuate slot.

The rivet 114 (FIG. 1) is generally similar to the rivet 66 and, therefore, will not be described in detail. The rivet 114 has a first portion 116 and a second portion 118. The first portion 116 has a shaft 120 extending from a head 122. The shaft 120 extends through the slot 100 and the head 122 engages a washer 124. A cylindrical opening 126 extends through the shaft 120 and the head 122.

The second portion 118 of the rivet 114 has a shaft 128 extending from a head 130. The shaft 128 extends into the opening 126 in the first portion 116 of the rivet 114 and the head 130 engages the outer surface 92 of the second tubular portion 40. The shaft 120 extends into the opening 126 to connect the first portion 116 of the rivet 114 to the second portion 118.

The second tubular portion 40 of the tubular structure 12 is expandable from a contracted condition, shown in FIG. 2, to any one of three expanded conditions, one of which is shown in FIG. 1. In the contracted condition, the guide member 114 is located in the first end 102 of the arcuate slot 100 in the second tubular portion 40. The second passage portion 94 defined by the second tubular portion 40 is cylindrical in shape. The second passage portion 94 has a generally constant diameter D2 which is approximately equal to the diameter D1 of the first tubular portion 20. Thus, the cross-sectional area of the second passage portion 94 at the second end 62 of the second tubular portion 40 is approximately the same as the cross-sectional area at the first end 60 of the second tubular portion and is approximately the same as the cross-sectional area of the first passage portion 30 in the first tubular portion 20.

In the expanded conditions (FIG. 1), the guide member 114 engages one of the stops 106 and is located in one of the notches 106 in the arcuate slot 100 in the second tubular portion 40. It is also contemplated that the guide member 114 could engage one of the stops 106 and be located between adjacent notches 106. The stops 106 retain the guide member 114 in one of a plurality of positions relative to the slot 100 and resist movement of the guide member from one of the plurality of positions relative to the slot. Accordingly, the stops 106 resist contraction of the second tubular portion 40.

Figure 5:
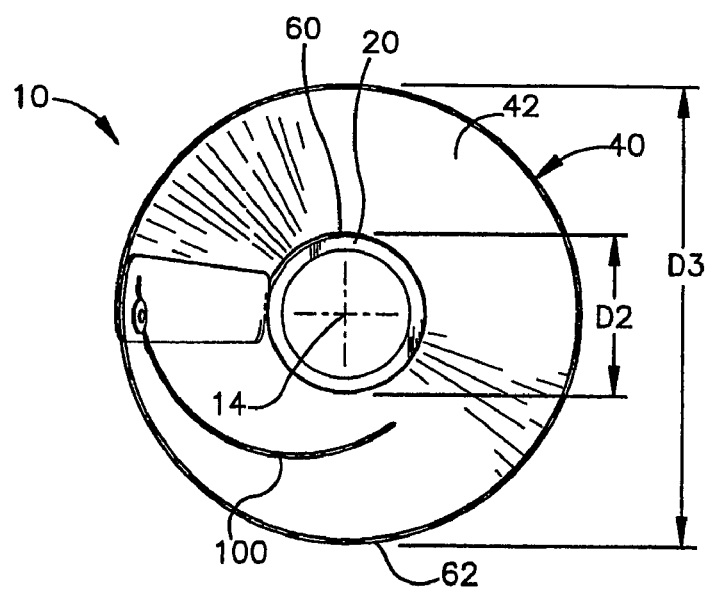
FIG. 5 is a schematic end view showing the cannula of FIG. 1 in the expanded condition.

The second tubular portion 40 has a conical configuration when in the expanded conditions. At the second end 62 (FIG. 5) of the second tubular portion 40, the second passage portion 94 has a diameter D3 which is larger than the diameter D2 of the second passage portion at the first end 60. Thus, in the expanded conditions, the cross-sectional area of the second passage portion 94 at the second end 62 of the second tubular portion 40 is greater than the cross-sectional area of the second passage portion at the first end 60 of the second tubular portion.

The cannula 10 (FIGS. 1 and 2) may include an outer member (not shown) for maintaining the second tubular portion 40 of the cannula in the contracted condition. It is contemplated that other suitable means for maintaining the second tubular portion 40 in the contracted condition could be employed. The outer member may be a layer of plastic tubing which is heat shrunk over both the first and second tubular portions 20 and 40 to hold the second tubular portion in the contracted condition. In addition, a loop of nylon string (not shown) for tearing the heat shrink tubing is wrapped around the heat shrink tubing so that it extends both underneath and on top of the tubing. An outer end of the string extends beyond the tubing.

Figure 6:
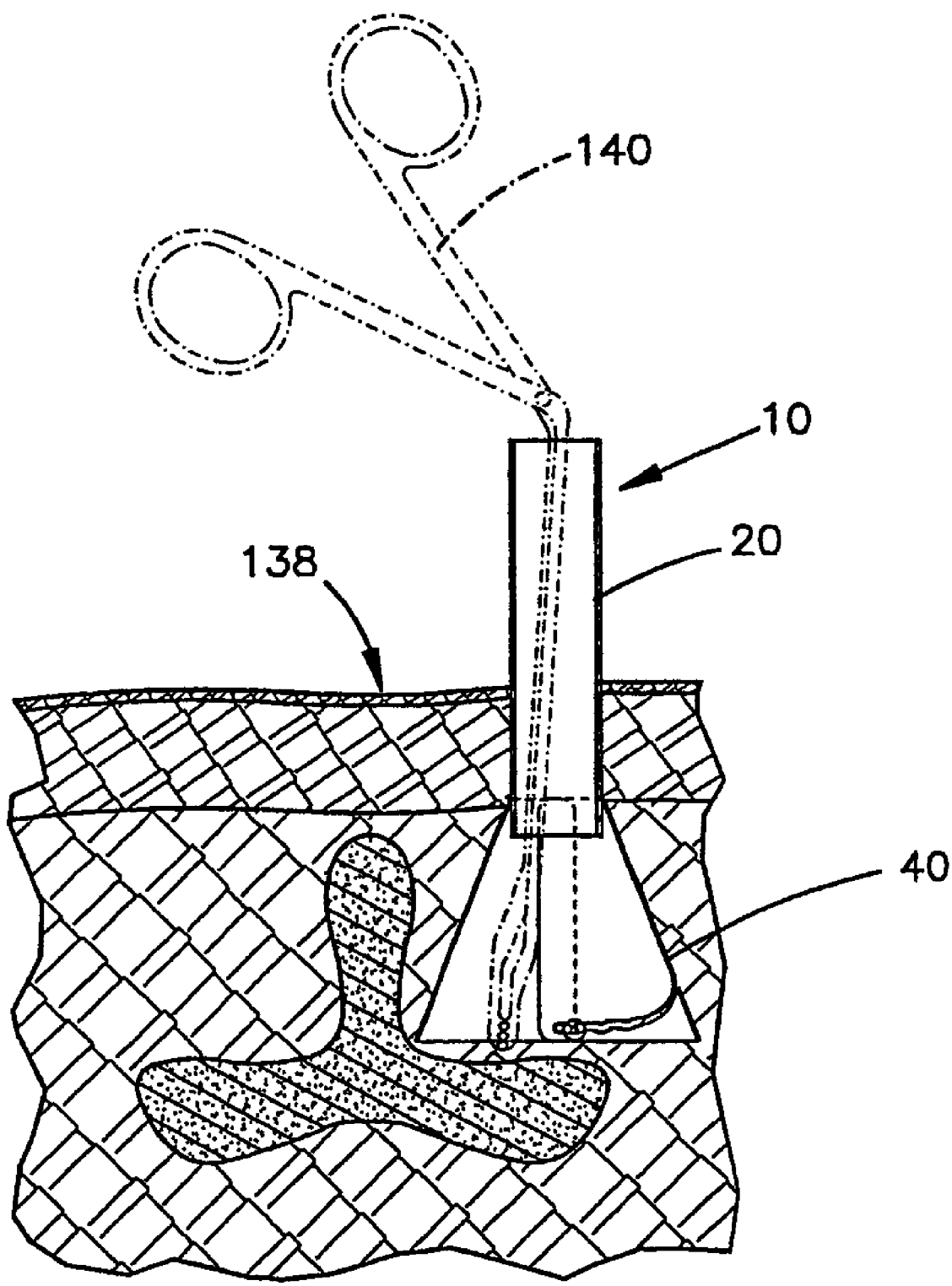
FIG. 6 is a schematic sectional view of the cannula of FIG. 1 adjacent a vertebra[e ]of a patient's spine during a surgical procedure.

During an endoscopic surgical procedure, the cannula 10 (FIG. 6) is inserted through an incision into a body 138 of a patient in the contracted condition. The second tubular portion 40 is inserted inside the body 138. The first tubular portion 20 is inserted into the incision so that the first tubular portion extends from an exterior of the body 138 to inside the body.

The outer end of the string is then manually pulled on by the surgeon. Pulling on the string tears the heat shrink tubing.

The heat shrink tubing remains on the cannula 10. With the heat shrink tubing torn, the second tubular portion 40 of the cannula 10 is thereby released for expansion toward one of the expanded conditions.

Next, an expansion tool (not shown) is inserted into the passage 16 in the cannula 10. The expansion tool is manually operated, causing a radially outwardly directed force to be exerted on the inner surface 90 of the second tubular portion 40 by the tool. The second tubular portion 40 expands toward one of the expanded conditions. Under the force of the expansion tool, the guide member 114 slides from the first end 102 of the arcuate slot 100 toward the second end 102 of the arcuate slot to permit the expansion of the second tubular portion 40. The guide member 114 engages a first stop 106 to position the guide member relative to the slot 100. If the second tubular portion 40 needs to be expanded further, additional force is applied to the second tubular portion to move the guide member 114. Expansion of the second tubular portion 40 can be stopped when the guide member 114 engages one of the stops 106. The guide member 114 engages the stops 106 to position the guide member in any one of the plurality of positions relative to the slot 100. The stops 106 resist movement of the guide member 114 relative to the slot 100. Accordingly, the second tubular portion 40 has a plurality of expanded conditions. The expansion tool is then removed so that one or more surgical instruments (indicated schematically at 140 in FIG. 6) can be received through the cannula 10 and inserted into a patient's body 138.

The expandable second tubular portion 40 of the cannula 10 provides a large working area for the surgeon inside the body 140 within the confines of the cannula. Furthermore, the second tubular portion 40 provides a working area that is only as large as needed. As a result, the simultaneous use of a number of endoscopic surgical instruments, including but not limited to steerable instruments, shavers, dissectors, scissors, forceps, retractors, dilators, and video cameras, is made possible by the expandable cannula 10.

A cannula 210 constructed according to a second embodiment of the present invention is illustrated in FIGS. 7-8. The cannula 210 includes a tubular structure 212. The tubular structure 212 defines a passage 216 through the cannula 210. Surgical instruments are inserted into the body during endoscopic surgery through the passage 216.

The tubular structure 212 comprises a first tubular portion 220 and a second tubular portion 240 attached to the first tubular portion. The first tubular portion 220 is identical to the first tubular portion 20 described in connection with the embodiment disclosed in FIGS. 1-6. Accordingly, the first tubular portion 220 will not be described in detail.

The second tubular portion 240 of the tubular structure 212 is attached to a distal end 224 of the first tubular portion 220. As best seen in the rollout view of FIG. 8, the second tubular portion 240 includes an arcuate segment 242 of sheet stock. The arcuate segment 242 includes first and second edges 244 and 246. The arcuate segment 242 also includes first and second planar edges 248 and 250 extending between the edges 244 and 246. The first and second planar edges 248 and 250 are rolled in an overlapping manner to form the tubular configuration of the second tubular portion 240.

When the second tubular portion 240 has been rolled into its tubular configuration, the first and second arcuate edges 244 and 246 define oppositely disposed first and second ends 260 and 262 (FIG. 7) of the second tubular portion. The first and second ends 260 and 262 are connected by a central portion 264. The first end 260 of the second tubular portion 240 is attached to the distal end 224 of the first tubular portion 220 by a suitable fastener, such as a rivet 266. The rivet 266 extends through two aligned apertures 268 (FIG. 8) at the first end 260 of the second tubular portion 240. The rivet 266 is identical to the rivet 66 described in connection with the embodiment illustrated in FIGS. 1-6. Accordingly, the rivet 266 will not be described in detail.

The second tubular portion 240 (FIG. 7) includes parallel inner and outer surfaces 290 and 292 extending between the first and second ends 260 and 262. The inner surface 290 defines a second passage portion 294 of the passage 216 through the cannula 210 which extends as a continuation of a first passage portion 230 in the first tubular portion 220.

An arcuate slot 270 (FIGS. 7 and 8) is formed in the second tubular portion 240 and extends between the inner and outer surfaces 290 and 292 of the second tubular portion. The arcuate slot 270 extends in a direction along a curvilinear path in the central portion 264 of the second tubular portion 240 toward the end 262 of the second tubular portion. The arcuate slot 270 has a first end 272 located in the central portion 264 of the second tubular portion 240. A second end 274 of the arcuate slot 270 is located adjacent the intersection of the second edge 246 and the planar edge 248 of the arcuate segment 242.

A guide member or tab 280 extends from the second tubular portion 240 at a location adjacent the intersection of the second edge 246 and the planar edge 250 of the arcuate segment 242. The tab 280 is formed by bending a cut-out of the arcuate segment 242 to extend through the slot 270. In the tubular configuration of the second tubular portion 240, the tab 280 is located in the arcuate slot 270 and is movable along the curvilinear path of the arcuate slot.

The second tubular portion 240 of the tubular structure 212 is expandable from a contracted condition to an expanded condition. In the contracted condition, the guide member 280 is located in the first end 272 of the arcuate slot 270 in the second tubular portion 240. The second passage portion 294 defined by the second tubular portion 240 is cylindrical in shape. The second passage portion 294 has a generally constant diameter which is approximately equal to the diameter of the first tubular portion 220. Thus, the cross-sectional area of the second passage portion 294 at the second end 262 of the second tubular portion 240 is approximately the same as a cross-sectional area at the first end 260 of the second tubular portion and is approximately the same as a cross-sectional area of the first passage portion 230 in the first tubular portion 220.

In the expanded condition, the guide member 280 is located in the second end 274 of the arcuate slot 270 in the second tubular portion 240. The second tubular portion 240 has a conical configuration. At the second end 262 of the second tubular portion 240, the second passage portion 294 has a diameter which is larger than the diameter of the second passage portion at the first end 260. Thus, in the expanded condition, the cross-sectional area of the second passage portion 294 at the second end 262 of the second tubular portion 240 is greater than the cross-sectional area of the second passage portion at the first end 260 of the second tubular portion.

During an endoscopic surgical procedure, the cannula 210 is inserted through an incision into the body of a patient in the contracted condition. The second tubular portion 240 is inserted inside the body. The first tubular portion 220 is inserted into the incision so that the first tubular portion extends from an exterior of the body to inside the body.

An expansion tool (not shown) is inserted into the passage 216 in the cannula 210. The expansion tool is manually operated, causing a radially outwardly directed force to be exerted on the inner surface 290 of the second tubular portion 240 by the tool. The second tubular portion 240 expands toward the expanded condition. Under the force of the expansion tool, the guide member 280 slides from the first end 272 of the arcuate slot 270 to the second end 274 of the arcuate slot to permit the expansion of the second tubular portion 240. The expansion tool is then removed so that one or more surgical instruments can be received through the cannula 210 and inserted into a patient's body.

The expandable second tubular portion 240 of the cannula 210 provides a large working area for the surgeon inside the body within the confines of the cannula. As a result, simultaneous use of a number of endoscopic surgical instruments, including but not limited to steerable instruments, shavers, dissectors, scissors, forceps, retractors, dilators, and video cameras, is made possible by the expandable cannula 210.

Figure 9:
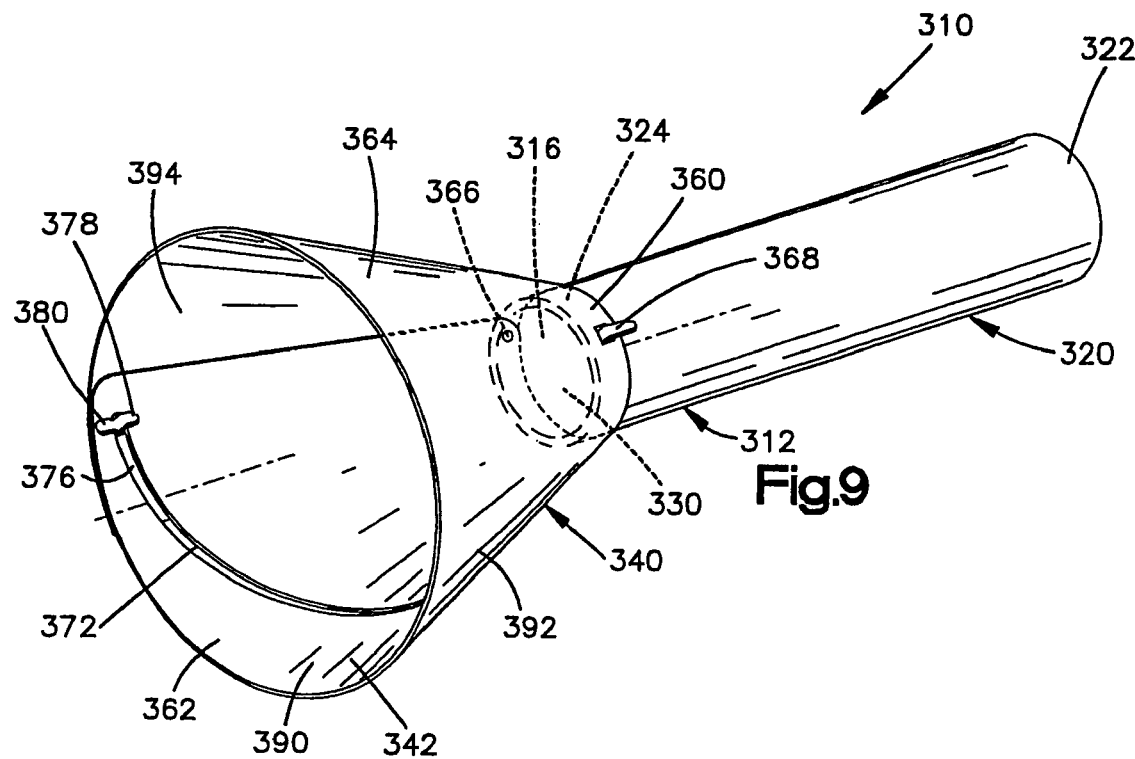
FIG. 9 is a schematic perspective view of a surgical cannula constructed in accordance with a third embodiment of the present invention, the cannula being shown in an expanded condition.
Figure 10:
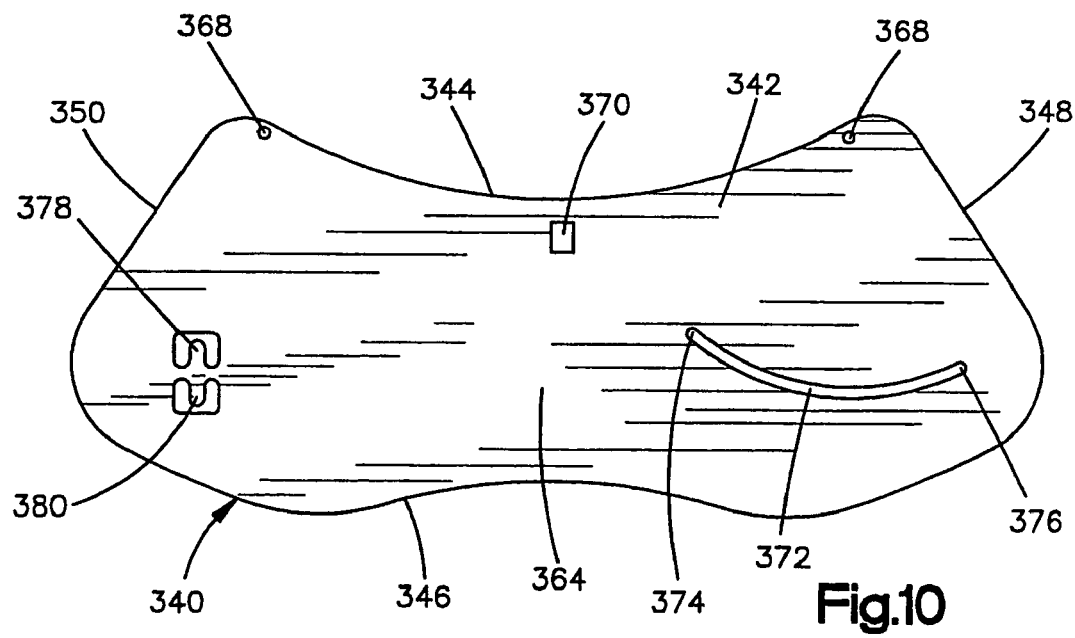
FIG. 10 is a rollout view of an arcuate segment of the cannula of FIG. 9.

A cannula 310 constructed according to a third embodiment of the present invention is illustrated in FIGS. 9-10. The cannula 310 includes a tubular structure 312. The tubular structure 312 defines a passage 316 through the cannula 310. Surgical instruments are inserted into the body during endoscopic surgery through the passage 316.

The tubular structure 312 comprises a first tubular portion 320 and a second tubular portion 340 attached to the first tubular portion. The first tubular portion 320 has a proximal end 322 and a distal end 324. Parallel cylindrical inner and outer surfaces extend between the ends 322 and 324 of the first tubular portion 320. The inner surface defines a first passage portion 330 of the passage 316 through the cannula 310.

The second tubular portion 340 of the tubular structure 312 is attached to the distal end 324 of the first tubular portion 320. As best seen in the rollout view of FIG. 10, the second tubular portion 340 includes an arcuate segment 342 of sheet stock. The arcuate segment 342 includes first and second edges 344 and 346. The arcuate segment 342 also includes first and second planar edges 348 and 350 extending between the edges 344 and 346. The first and second planar edges 348 and 350 are rolled in an overlapping manner to form the tubular configuration of the second tubular portion 340.

When the second tubular portion 340 (FIG. 9) has been rolled into its tubular configuration, the first and second arcuate edges 344 and 346 define oppositely disposed first and second ends 360 and 362 of the second tubular portion. The first and second ends 360 and 362 are connected by a central portion 364. The first end 360 of the second tubular portion 340 is attached to the distal end 324 of the first tubular portion 320 by a suitable fastener, such a rivet 366.

The rivet 366 is identical to the rivet 66 described in connection with the embodiment illustrated in FIGS. 1-6. Accordingly, the rivet 366 will not be described in detail. The rivet 366 extends through aligned apertures 368 (FIG. 10) at the first end 360 of the second tubular portion 340.

The first end 360 (FIGS. 9 and 10) of the second tubular portion 340 is also attached to the distal end 324 of the first tubular portion 320 by a tab 368 extending from the distal end 324 of the first tubular portion 320. The tab 368 extends through an opening 370 in the second tubular portion 340 and is bent over to connect the second tubular portion to the first tubular portion 320. The end of the tab 368 extending through the opening 370 may also be spot welded, soldered, or braized to the first tubular portion 320.

The second tubular portion 340 includes parallel inner and outer surfaces 390 and 392 extending between the first and second ends 360 and 362. The inner surface 390 defines a second passage portion 394 of the passage 316 through the cannula 310 which extends as a continuation of the first passage portion 330 in the first tubular portion 320.

An arcuate slot 372 is formed in the second tubular portion 340 and extends between the inner and outer surfaces 390 and 392 of the second tubular portion. The arcuate slot 372 extends along a curvilinear path in the central portion 364 of the second tubular portion 340 toward the end 362 of the second tubular portion. The arcuate slot 372 has a first end 374 located in the central portion 364 of the second tubular portion 340. A second end 376 of the arcuate slot 372 is located adjacent the intersection of the second edge 346 and the planar edge 348 of the arcuate segment 342.

Guide members or tabs 378 and 380 extend from the second tubular portion 340 adjacent the intersection of the second edge 346 and the planar edge 350 of the arcuate segment 342. The tabs 378 and 380 are formed by bending cut-outs of the arcuate segment 342 to extend through the slot 370. In the tubular configuration of the second tubular portion 340, the tabs 378 and 380 are located in the arcuate slot 372 and are movable along the curvilinear path of the arcuate slot.

The second tubular portion 340 of the tubular structure 312 is expandable from a contracted condition to an expanded condition. In the contracted condition, the tabs 378 and 380 are located in the first end 374 of the arcuate slot 372 in the second tubular portion 340. The second passage portion 394 defined by the second tubular portion 340 is cylindrical in shape. The second passage 394 has a generally constant diameter which is approximately equal to the diameter of the first tubular portion 320. Thus, the cross-sectional area of the second passage portion 394 at the second end 362 of the second tubular portion 340 is approximately the same as the cross-sectional area at the first end 360 of the second tubular portion and is approximately the same as the cross-sectional area of the first passage portion 330 in the first tubular portion 320.

In the expanded condition, the tabs 378 and 380 are located in the second end 376 of the arcuate slot 372 in the second tubular portion 340. The second tubular portion 340 has a conical configuration. At the second end 362 of the second tubular portion 340, the second passage portion 394 has a diameter which is larger than the diameter of the second passage portion at the first end 360. Thus, in the expanded condition, the cross-sectional area of the second passage portion 394 at the second end 362 of the second tubular portion 340 is greater than the cross-sectional area of the second passage portion at the first end 360 of the second tubular portion.

During an endoscopic surgical procedure, the cannula 310 is inserted through an incision into the body of a patient in the contracted condition. The second tubular portion 340 is inserted inside the body. The first tubular portion 320 is inserted into the incision so that the first tubular portion extends from an exterior of the body to inside the body.

An expansion tool (not shown) is inserted into the passage 316 in the cannula 310. The expansion tool is manually operated, causing a radially outwardly directed force to be exerted on the inner surface 390 of the second tubular portion 340 by the tool. The second tubular portion 340 expands toward the expanded condition. Under the force of the expansion tool, the tabs 378 and 380 slide from the first end 374 of the arcuate slot 372 to the second end 376 of the arcuate slot to permit the expansion of the second tubular portion 340.

The expandable second tubular portion 340 of the cannula 310 provides a large working area for the surgeon inside the body within the confines of the cannula. As a result, the simultaneous use of a number of endoscopic surgical instruments is made possible by the expandable cannula 310.

Figure 11:
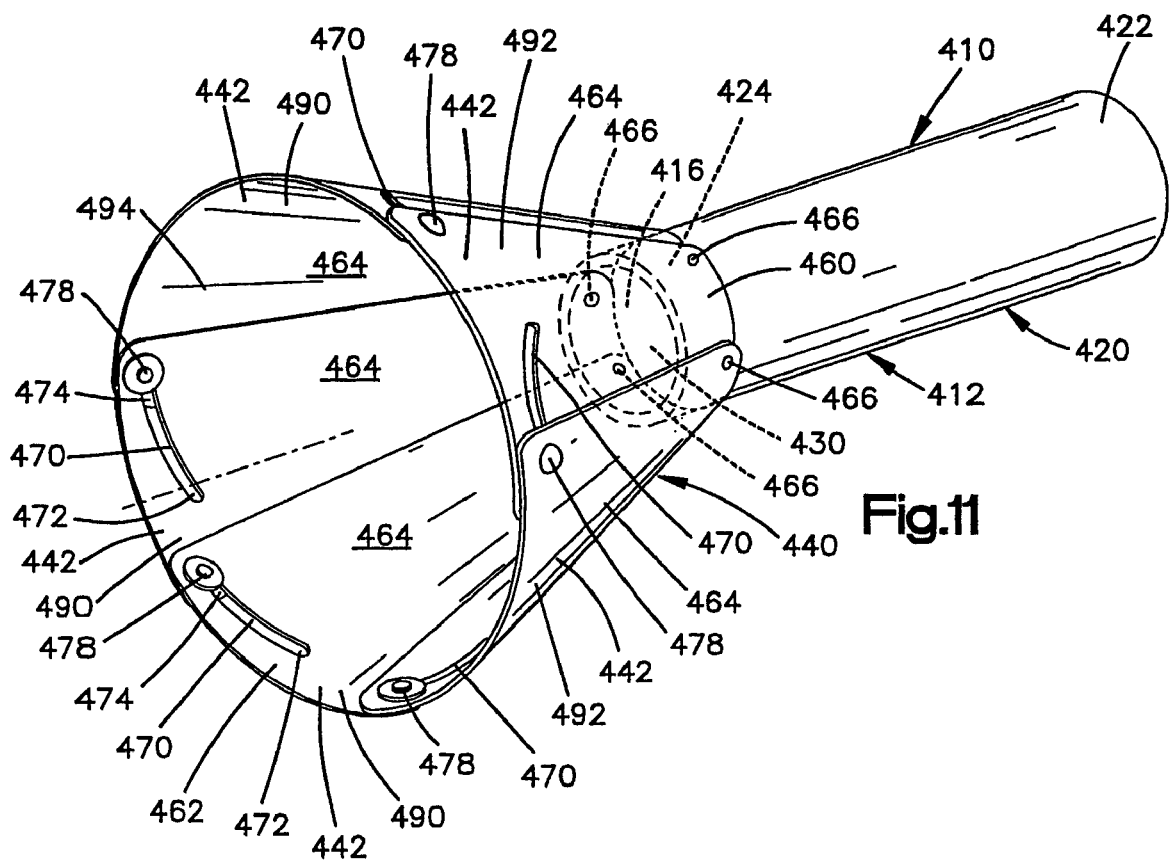
FIG. 11 is a schematic perspective view of a surgical cannula constructed in accordance with a fourth embodiment of the present invention, the cannula being shown in an expanded condition.
Figure 12:
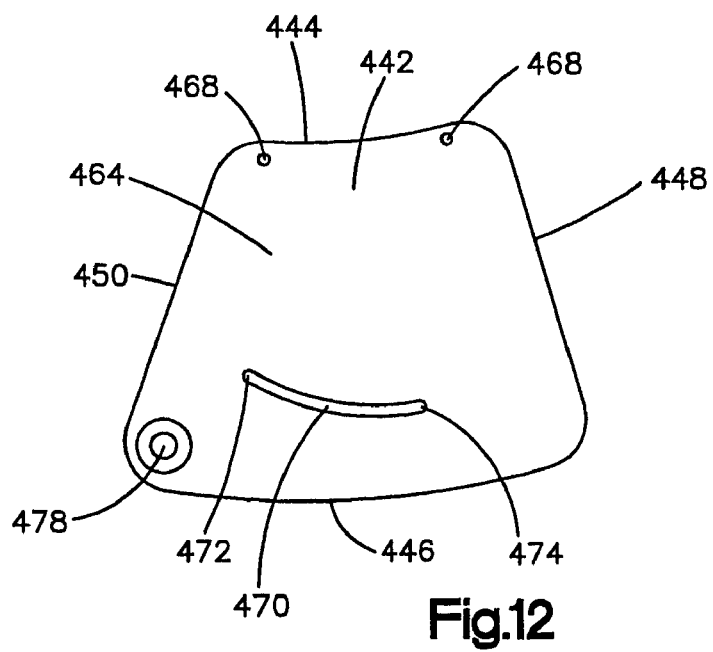
FIG. 12 is an enlarged rollout view of an arcuate segment of the cannula of FIG. 11.

A cannula 410 constructed according to a fourth embodiment of the present invention is illustrated in FIGS. 11-12.

The cannula 410 includes a tubular structure 412. The tubular structure 412 defines a passage 416 through the cannula 410. Surgical instruments are inserted into the body during endoscopic surgery through the passage 416.

The tubular structure 412 comprises a first tubular portion 420 and a second tubular portion 440 attached to the first tubular portion. The first tubular portion 420 has a proximal end 422 and a distal end 424. Parallel cylindrical inner and outer surfaces extend between the ends 422 and 424 of the first tubular portion 420. The inner surface defines a first passage portion 430 of the passage 416 through the cannula 410.

The second tubular portion 440 of the tubular structure 412 is attached to the distal end 424 of the first tubular portion 420. The second tubular portion 440 includes a plurality of arcuate segments 442 of sheet stock. The present invention has five arcuate segments 442. However, it is contemplated that any number of arcuate segments 442 could be used.

The arcuate segments 442 are identical. Accordingly, only one of the arcuate segments 442 will be described in detail. The arcuate segment 442 (FIG. 12) includes first and second arcuate edges 444 and 446. The arcuate segment 442 also includes first and second planar edges 448 and 450 extending between the arcuate edges 444 and 446. The planar edges 448 and 450 of the arcuate segments 442 overlap each other to form the tubular configuration of the second tubular portion 440.

When the second tubular portion 440 (FIGS. 11-12) is in its tubular configuration, the arcuate edges 444 and 446 define oppositely disposed first and second ends 460 and 462 of the second tubular portion. The first and second ends 460 and 462 are connected by central portions 464 of the arcuate segments 442. The first end 460 of the second tubular portion 440 is attached to the distal end 424 of the first tubular portion 420 by suitable fasteners, such as rivets 466. The rivets 466 extend through aligned apertures 468 at the first end 460 of the second tubular portion 440.

Each of the arcuate segments 442 includes parallel inner and outer surfaces 490 and 492 extending between the first and second ends 460 and 462 of the second tubular portion 440. The inner surfaces 490 define a second passage portion 494 of the passage 416 through the cannula 410 which extends as a continuation of the first passage portion 430 in the first tubular portion 420.

Arcuate slots 470 are formed in the arcuate segments 442 and extend between the inner and outer surfaces 490 and 492 of the second tubular portion 440. The arcuate slots 470 extend along curvilinear paths in the central portions 464 of the arcuate segments 442 toward the end 462 of the second tubular portion. The arcuate slots 470 have first ends 472 located in the central portions 464. Second ends 474 of the arcuate slots 470 are located adjacent the end 462 of the second tubular portion 440. Guide members or rivets 478 are attached to the arcuate segments 442. The guide members 478 are identical to the guide member 114 described in connection with the embodiment illustrated in FIGS. 1-6. Accordingly, the guide members 478 will not be described in detail. In the tubular configuration of the second tubular portion 440, the guide members 478 are located in the arcuate slots 470 and are movable along the curvilinear paths of the arcuate slots.

The second tubular portion 440 of the tubular structure 412 is expandable from a contracted condition to an expanded condition. In the contracted condition, the guide members 478 are located in the first ends 472 of the arcuate slots 470 in the second tubular portion 440. The second passage portion 494 defined by the second tubular portion 440 is cylindrical in shape. The second passage 494 has a generally constant diameter which is approximately equal to the diameter of the first tubular portion 420. Thus, the cross-sectional area of the second passage portion 494 at the second end 462 of the second tubular portion 440 is approximately the same as the cross-sectional area at the first end 460 of the second tubular portion and is approximately the same as the cross-sectional area of the first passage portion 430 in the first tubular portion 420.

In the expanded condition, the guide members 478 are located in the second ends 474 of the arcuate slots 470 in the second tubular portion 440. The second tubular portion 440 has a conical configuration. At the second end 462 of the second tubular portion 440, the second passage portion 494 has a diameter which is larger than the diameter of the second passage portion at the first end 460. Thus, in the expanded condition, the cross-sectional area of the second passage portion 494 at the second end 462 of the second tubular portion 440 is greater than the cross-sectional area of the second passage portion at the first end 460 of the second tubular portion.

During an endoscopic surgical procedure, the cannula 410 is inserted through an incision into the body of a patient in the contracted condition. The second tubular portion 440 is inserted inside the body. The first tubular portion 420 is inserted into the incision so that the first tubular portion extends from an exterior of the body to inside the body.

An expansion tool (not shown) is inserted into the passage 416 in the cannula 410. The expansion tool is manually operated, causing a radially outwardly directed force to be exerted on the inner surfaces 490 of the second tubular portion 440 by the tool. The second tubular portion 440 expands toward the expanded condition. Under the force of the expansion tool, the guide members 478 slide from the first ends 472 of the arcuate slots 470 to the second ends 474 of the arcuate slots to permit the expansion of the second tubular portion 440.

The expandable second tubular portion 440 of the cannula 410 provides a large working area for the surgeon inside the body within the confines of the cannula. As a result, the simultaneous use of a number of endoscopic surgical instruments is made possible by the expandable cannula 410. Although the slots 470 are shown as not having stops, it is contemplated that the slots could have stops or notches similar to the stops 106 described in connection with the embodiment illustrated in FIGS. 1-6.

Figure 13:
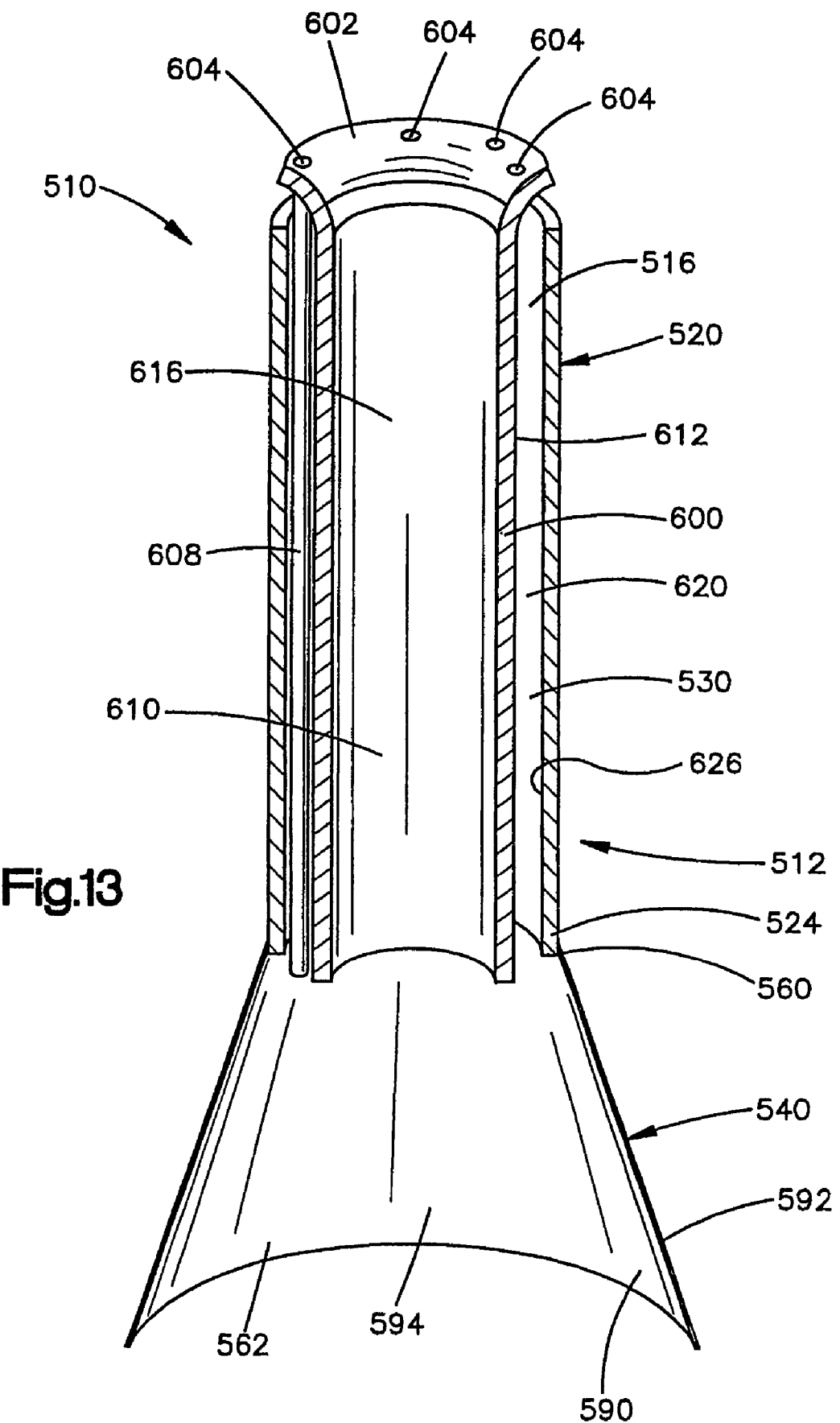
FIG. 13 is a schematic sectional view of a surgical cannula constructed in accordance with a fifth embodiment of the present invention.

A cannula 510 constructed according to a fifth embodiment of the present invention is illustrated in FIG. 13. The cannula 510 includes a tubular structure 512. The tubular structure 512 defines a passage 516 through the cannula 510. Surgical instruments are inserted into the body during endoscopic surgery through the passage 516.

The tubular structure 512 comprises a first tubular portion 520 and a second tubular portion 540 attached to the first tubular portion. The first and second tubular portions 520 and 540 are identical to the first and second tubular portions 20 and 40 described in connection with the embodiment disclosed in FIGS. 1-6. Accordingly, the first and second tubular portions 520 and 540 will not be described in detail.

The second tubular portion 540 of the tubular structure 512 is attached to a distal end 524 of the first tubular portion 520. A first end 560 of the second tubular portion 540 is attached to the distal end 524 of the first tubular portion 520 by a suitable fastener (not shown), such as a rivet. The second tubular portion 540 includes parallel inner and outer surfaces 590 and 592 extending between first and second ends 560 and 562. The inner surface 590 defines a second passage portion 594 of the passage 516 through the cannula 510 which extends as a continuation of a first passage portion 530 in the first tubular portion 520.

The second tubular portion 540 of the tubular structure 512 is expandable from a contracted condition to an expanded condition. In the contracted condition, the second passage portion 594 defined by the second tubular portion 540 is cylindrical in shape. The second passage portion 594 has a generally constant diameter which is approximately equal to the diameter of the first tubular portion 520. Thus, the cross-sectional area of the second passage portion 594 at the second end 562 of the second tubular portion 540 is approximately the same as a cross-sectional area at the first end 560 of the second tubular portion and is approximately the same as a cross-sectional area of the first passage portion 530 in the first tubular portion 520.

In the expanded condition, the second tubular portion 540 has a conical configuration. At the second end 562 of the second tubular portion 540, the second passage portion 594 has a diameter which is larger than the diameter of the second passage portion at the first end 560. Thus, in the expanded condition, the cross-sectional area of the second passage portion 594 at the second end 562 of the second tubular portion 540 is greater than the cross-sectional area of the second passage portion at the first end 560 of the second tubular portion.

A second tubular structure 600 extends into the first tubular portion 520 of the tubular structure 512. The second tubular portion 600 extends into the first passage portion 530. The second tubular structure 600 has a radially extending flange 602 with openings 604 for receiving endoscopic surgical instruments and/or for application of suction or irrigation fluid. A tube 608 may extend from the flange 602 adjacent one of the openings 604 for receiving a surgical instrument and/or the application of suction or irrigation fluid.

The second tubular structure 600 includes parallel inner and outer surfaces 610 and 612. The inner surface 610 defines a passage 616 through the second tubular structure 600. The outer surface 612 and the inner surface 626 of the first tubular portion 520 define an annular passage 620. The openings 604 in the flange 602 of the second tubular structure 600 communicate with the annular passage 620. Accordingly, surgical instruments extend through the openings 604 into the annular passage 620.

During an endoscopic surgical procedure, the cannula 510 is inserted through an incision into the body of a patient in the contracted condition. The second tubular portion 540 is inserted inside the body. The first tubular portion 520 is inserted into the incision so that the first tubular portion extends from an exterior of the body to inside the body.

Next, an expansion tool (not shown) is inserted into the passage 516 in the cannula 510. The expansion tool is manually operated, causing a radially outwardly directed force to be exerted on the inner surface 590 of the second tubular portion 540 by the tool. The second tubular portion 540 expands toward the expanded condition. The expansion tool is then removed so that the second tubular structure 600 may be inserted into the passage 516.

The second tubular structure 600 is inserted into the passage 516 to define the annular passage 620. Surgical instruments can be received through the openings 604 in the flange 602 and into the annular passage 620 and one or more surgical instruments can be received through the passage 616 and/or suction or irrigation fluid can be applied through the passage 616. As a result, the simultaneous use of a number of endoscopic surgical instruments is made possible by the cannula 510.

From the above description of the invention, those skilled in the art will perceive improvements, changes and modifications. Such improvements, changes and modifications within the skill of the art are intended to be covered by the appended claims.

Having described the invention, the following is claimed:

1. A method for retracting tissue adjacent a spinal location, comprising:
   making an incision in a patient over a spinal surgical location;
   inserting a retractor into the incision in the patient;
   advancing the retractor to a position adjacent the spinal location, the retractor having a proximal end and a distal end and defining an access path therethrough, the distal end being positioned adjacent the spinal location and the proximal end extending through the incision and outside of the patient;
   expanding at least a portion of the retractor adjacent the spinal location by moving a plurality of discrete segments of the retractor away from each other to retract tissue adjacent the spinal location, wherein the discrete segments at least partially surround said access path in the expanded configuration; and
   performing a surgical procedure on the spine, wherein the surgical procedure is performed through the retractor.

2. The method of claim 1, wherein expanding at least a portion of the retractor comprises moving at least three discrete segments of the retractor away from each other.

3. The method of claim 1, wherein expanding at least a portion of the retractor comprises moving at least four discrete segments of the retractor away from each other.

4. The method of claim 1, wherein expanding at least a portion of the retractor comprises moving five discrete segments of the retractor away from each other.

5. The method of claim 1, wherein each of the discrete segments comprises an arcuate edge.

6. The method of claim 1, wherein expanding at least a portion of the retractor causes a cross-sectional area of the access path at the distal end to be larger than a cross-sectional area of the access path at the proximal end.

7. The method of claim 1, further comprising delivering a plurality of instruments simultaneously through the access path to perform the surgical procedure at the spinal location.

8. The method of claim 1, wherein overlap exists between discrete segments in an unexpanded configuration, and wherein expanding at least a portion of the retractor comprises reducing overlap between adjacent discrete segments.

9. The method of claim 1, wherein each of the discrete segments is made of a sheet material.

10. A method for retracting tissue adjacent a spinal location, comprising:
    making an incision in a patient over a spinal location;
    inserting a retractor into the incision;
    positioning the retractor in the patient adjacent the spinal location, the retractor having a proximal portion and a distal portion;
    pivoting the distal portion relative to the proximal portion; and
    expanding at least a portion of the distal portion adjacent the spinal location by moving a plurality of discrete segments of the retractor away from each other to retract tissue adjacent the spinal location; wherein overlap exists between discrete segments in an unexpanded and an expanded configuration, and wherein expanding at least a portion of the retractor comprises reducing overlap between adjacent discrete segments.

11. The method of claim 10, wherein expanding at least a portion of the retractor comprises moving at least three discrete segments of the retractor away from each other.

12. The method of claim 10, wherein expanding at least a portion of the retractor comprises moving at least four discrete segments of the retractor away from each other.

13. The method of claim 10, wherein expanding at least a portion of the retractor comprises moving five discrete segments of the retractor away from each other.

14. The method of claim 10, wherein each of the discrete segments comprises an arcuate edge.

15. The method of claim 10, further comprising delivering a plurality of instruments simultaneously through the retractor to perform the procedure at the spinal location.

16. The method of claim 10, wherein each of the discrete segments is made of a sheet material.

17. The method of claim 10, wherein expanding at least a portion of the retractor causes a cross-sectional area of the retractor at a first location to be larger than a cross-sectional area of the access path at a second location proximal of the first location.

18. A method for retracting tissue adjacent a spinal location, comprising:

making an incision in a patient over a spinal surgical location;

inserting a retractor into the incision in the patient;

advancing the retractor to a position adjacent the spinal location, the retractor having a proximal end and a distal end, the distal end having a plurality of discrete segments and being positioned adjacent the spinal location and the proximal end being positioned outside of the patient, the retractor having a guiding mechanism including a slot with notches extending transverse to a direction in which the slot extends; and expanding at least a portion of the retractor adjacent the spinal location by moving a plurality of discrete segments of the retractor away from each other to retract tissue adjacent the spinal location, wherein the discrete segments are moved away from each other by being guided incrementally along successive notches of the guiding mechanism.

19. The method of claim 18, wherein expanding at least a portion of the retractor comprises moving at least three discrete segments of the retractor away from each other.

20. The method of claim 18, wherein expanding at least a portion of the retractor comprises moving at least four discrete segments of the retractor away from each other.

21. The method of claim 18, wherein expanding at least a portion of the retractor comprises moving five discrete segments of the retractor away from each other.

22. The method of claim 18, wherein each of the discrete segments comprises an arcuate edge and a slot with notches.

23. The method of claim 18, wherein expanding at least a portion of the retractor causes a cross-sectional area of the retractor at the distal end to be larger than a cross-sectional area of the retractor at the proximal end.

24. The method of claim 18, further comprising delivering a plurality of instruments simultaneously through the retractor to perform the procedure at the spinal location.

25. The method of claim 18, wherein overlap exists between discrete segments in an unexpanded configuration, and wherein expanding at least a portion of the retractor comprises reducing overlap between adjacent discrete segments.

26. The method of claim 18, wherein each of the discrete segments is made of a sheet material.

27. The method of claim 18, wherein each of said notches maintains a desired configuration of said retractor.

28. The method of claim 18, wherein each of said notches prevents the retractor from moving from an expanded configuration to a contracted configuration.

29. The method of claim 18, wherein the guiding mechanism comprises at least three notches.

* * * * *